United States Patent [19]
Hoelderich et al.

[11] Patent Number: 6,071,844
[45] Date of Patent: Jun. 6, 2000

[54] METHOD OF PRODUCING ε-CAPROLACTAM, MFI ZEOLITE CATALYSTS ON WHOSE SURFACE SYMMETRICALLY ARRANGED OH GROUPS ARE PRESENT AND TO A METHOD OF PRODUCING THEM

[75] Inventors: Wolfgang Hoelderich, Frankenthal; Joerg Roeseller, Aachen; Dietrich Arntz, Oberursel, all of Germany

[73] Assignee: Degussa-Hüls Aktiengesellschaft, Frankfurt, Germany

[21] Appl. No.: 08/970,436

[22] Filed: Nov. 14, 1997

Related U.S. Application Data

[62] Division of application No. 08/647,438, May 6, 1996, Pat. No. 5,741,904.

[30] Foreign Application Priority Data

May 4, 1995 [DE] Germany ............................ 195 16 284
Mar. 6, 1996 [DE] Germany ............................ 196 08 660

[51] Int. Cl.$^7$ ...................................................... B01J 29/06
[52] U.S. Cl. .................................. 502/77; 502/85; 502/86
[58] Field of Search ................................... 502/77, 85, 86

[56] References Cited

U.S. PATENT DOCUMENTS

| | | | |
|---|---|---|---|
| 4,871,702 | 10/1989 | Chang et al. ............................... | 502/86 |
| 5,212,302 | 5/1993 | Kitamura et al. ........................ | 540/536 |

*Primary Examiner*—Tom Dunn
*Attorney, Agent, or Firm*—Smith, Gambrell & Russell, LLP

[57] ABSTRACT

A method of producing ε-caprolactam from cyclohexanone in the gaseous phase using MFI catalysts on whose surface symmetrically arranged OH groups are present.

16 Claims, 6 Drawing Sheets

■ Conversion
○ Selectivity

METHOD OF PRODUCING ε-CAPROLACTAM, MFI ZEOLITE CATALYSTS ON WHOSE SURFACE SYMMETRICALLY ARRANGED OH GROUPS ARE PRESENT AND TO A METHOD OF PRODUCING THEM

This is a divisional of application Ser. No. 08/647,438, filed on May 6, 1996, now U.S. Pat. No. 5,741,904.

INTRODUCTION AND BACKGROUND

The present invention relates to an improved method of producing ε-caprolactam from cyclohexanone oxime in the gaseous phase using MFI catalysts on whose surface symmetrically arranged OH groups are present. The present invention also concerns such novel MFI catalysts on whose surface symmetrically arranged OH groups are present and to a method of producing them.

ε-Caprolactam is of great economic significance as the starting point for nylon-6-synthesis (Kirk-Other's *Encyclopedia of Chemical Technology*, (Third Edition), Volume 18, pages 425–436; this excerpt is entirely incorporated herein by reference). In the classic production method primarily used today, cyclohexanone oxime is converted on fuming sulfuric acid by the Beckmann rearrangement to ε-caprolactam (see, e.g., U.S. Pat. No. 4,968,793 which is incorporated by reference in its entirety). A disadvantage of this method is the use of ammonia which is necessary to neutralize the sulfuric acid and is associated with an accumulation of ammonium sulfate of up to 4.5 tons per ton caprolactam. In order to avoid this undesired byproduct, efforts have been undertaken since the middle of the 1960s to carry out the reaction by heterogeneous catalysis.

It is known that ε-caprolactam can be produced from cyclohexanone oxime in the gaseous phase on solid catalysts, e.g. on zeolites with MFI structure. The term MFI structure or topology is well known in the art (see, e.g., U.S. Pat. Nos. 5,374,747; 5,451,701; and 5,453,511, all of which are incorporated by reference in their entirety).

X and Y zeolites and mordenites in the H form or doped with rare earth metals or transition metals deactivate extremely rapidly. 5-Cyanopent-1-ene, cyclohexanone and cyclohexanol are formed increasingly as byproducts on these catalysts. Temperatures below 400° C. and atmospheric pressure have been suggested as process parameters. Furthermore, non-polar solvents such as cyclohexane, benzene or toluene are supposed to be more advantageous than more polar solvents.

The partial blocking of the acidic centers of the HY zeolite with Na did not result in an improvement of the results (M. Burquet et al., An. Quim. Ser. A 81 (1985) 259; A. Aucejo et al., Appl. Catal, 22 (1986) 187 and A. Corma et al., Zeolites 11 (1991) 593). Rather, the authors determined that strongly acidic Bronsted acidic centers with pKa<1.5 are necessary for the Beckmann rearrangement and that the selectivity-reducing byproduct 5-cyanopent-1-ene is formed both on the acidic centers and on the Na$^+$ ions. Furthermore, the authors suspected that the deactivation of the zeolite catalyst takes place by means of basic byproducts such as aniline and methylpyridine and not by coke formation on the catalyst surface since the color of the catalyst is still al most white after the reaction.

In order to avoid the disadvantages of the rapid ageing of X and Y zeolite catalysts, pentasil zeolites (MFI structure) have been extensively examined.

Zeolites with MFI structure are also favorably viewed in EP 0,494,535 (corresponding to U.S. Pat. Nos. 5,212,302 and 5,403,801 which are incorporated by reference in their entirety) and EP 0,544,530 (corresponding to U.S. Pat. No. 5,304,643 which is incorporated by reference in its entirety). However, a high Si/M ratio of 5 to over 500 is required here, which the metal (M) can be Al, B, Ga, among others. Alcohols and ethers as well as water are cited as additive components and solvents. The maximum addition of water is approximately 0.06 to 2.5 moles per mole oxime.

The attempts at improving the service life of the catalyst also took the direction that the outer surface of a boron-MFI zeolite was covered with Na ions in order in this manner to neutralize the acidity on the outer surface (EP 0,086,543 (Jul. 5, 1986) Stamicarbon; corresponding to U.S. Pat. No. 4,472,516 which is incorporated by reference in its entirety). A mixture of cyclohexanone oxime, toluene, carbon dioxide and water in a molar ratio of 1:3:7:1 at 340° C. is said to convert the cyclohexanone oxime quantitatively on this catalyst. The selectivity for ε-caprolactam is indicated as 58%. The service life of the catalyst treated with Na ions is approximately 15 hours and is more than three times as long as in the case of the untreated boron MFI zeolite. However, the byproduct 5-cyanopent-1-ene is also strongly formed on this catalyst and thus does not constitute a satisfactory result.

SUMMARY OF THE INVENTION

One object of the present invention is to solve the problem of improving the method of producing ε-caprolactam by means of the Beckmann rearrangement in the gaseous phase with the aid of modified zeolites of the MFI type as catalysts.

In achieving the above and other objects, one feature of the present invention resides in providing a method of producing ε-caprolactam by the Beckmann rearrangement of cyclohexanone oxime in the gaseous phase in a temperature range of 250° to 450° C. on zeolite catalysts wherein MFI zeolites are used on which OH groups are symmetrically arranged in relation to each other on the surface due to the lack of central metal atoms such as Si, Al and B.

Yet another feature of the present invention is a method of producing MFI zeolitic catalysts for use in producing ε-caprolactam. The method requires contacting a MFI zeolite having central metal atoms at a temperature of 20° to 150° C. under autogenous pressure in an autoclave with a solution of ammonia salts and/or aqueous ammonia solution to thereby remove some or all of the central metal atoms. The MFI zeolite catalysts have OH groups symmetrically arranged in relation to each other on the surface of the MFI zeolite catalysts due to the lack of central metal atoms. Another feature of the present invention is a MFI zeolitic catalyst for use in producing ε-caprolactam produced by that method.

Yet another feature of the present invention is a MFI zeolitic catalyst for use in producing ε-caprolactam which is a MFI zeolite having some or all of its central metal atoms removed, wherein the MFI zeolite catalyst has OH groups symmetrically arranged in relation to each other on the surface of the MFI zeolite catalyst due to the lack of central metal atoms.

BRIEF DESCRIPTION OF THE DRAWINGS

The present invention will be further understood with reference to the drawing, wherein.

DETAILED DESCRIPTION OF THE INVENTION

Crystalline silicates with MFI structure have long been known from the state of the art (see, e.g., U.S. Pat. Nos. 5,374,747; 5,451,701; and 5,453,511, all of which are incorporated by reference in their entirety). For example, they can be formed of only SiO$_4$ tetrahedrons; however, on the other hand, in the majority of them aluminosilicates are used as well as silicates in which other metal atoms instead of aluminum are present and inserted into the lattice skeleton.

The first synthesis of an aluminosilicate with MFI structure was published in U.S. Pat. No. 3,702,886 (which is incorporated by reference in its entirety), in which the designation "zeolite ZSM-5" was selected. It was classified for purposes of identification as pentasil zeolite. The areas of application include catalysis, molecular sieves or as drying agent. The composition of this zeolite class can be defined as follows:

$$0.9 \pm 0.2 M_{2/n}O : Al_2O_3 : 5-100 SiO_2 : zH_2O$$

in which M represents a cation, n is the charge of this cation, and z is a number between 0 and 40. The production of this catalyst type takes place in a hydrothermal synthesis. To this end, as a rule, a silicon source is dissolved with an aluminum source in the presence of water and of the template tetrapropylammonium hydroxide and brought to crystallization in an autoclave under agitation or static conditions.

Suitable conditions of synthesis bring about an isomorphous substitution of aluminum or silicon. Such skeleton-substituted zeolites with MFI structure contain e.g. tri- and bivalent elements such as e.g. B, Ga, Fe, Cr, Be, As, Sb and Bi instead of aluminum or tetravalent elements such as e.g. Ge, Ti, Zr, Hf instead of silicon.

This material generally receives catalytic properties by exchanging the sodium ions with e.g. protons or metallic cations.

A special embodiment of the production of zeolites is an alkali-free synthesis. The aluminosilicate zeolite can be produced e.g. from an aluminum compound, preferably Al(OH)$_3$ or Al$_2$(SO$_4$)$_3$, and from a silicon component, preferably highly dispersed silicon dioxide in aqueous amine solution, especially 1,6-hexane diamine- or 1,3-propane diamine- or triethylene triamine solution with or without the addition of alkali or alkaline earth metals at 100° to 200° C. under autogenous pressure. The aluminosilicates obtained in this manner contain, depending on the selection of the amounts of feed material, an SiO$_2$/Al$_2$O$_3$ ratio of 10 to 40,000. Such productions are described e.g. in EP 0,007,081. The aluminosilicate zeolites can also be produced in an ethereal medium such as e.g. diethyleneglycol dimethylether or 1,4-butane diol or in water.

The borosilicate zeolite can be synthesized e.g. at 900 to 200° C. under autogenous pressure by bringing a boron compound, e.g. H$_3$BO$_3$, to a reaction with a silicon compound, preferably highly dispersed silicon dioxide, in aqueous amine solution, especially in 1,6-hexane diamine- or 1,3-propane diamine- or triethylene tetramine solution with and especially without the addition of alkali or alkaline earth metals. This is described e.g. in EP 0,007,081. Instead of an aqueous amine solution, an ethereal solution can be used as solvent in this reaction, e.g. with diethyleneglycoldimethylether, or an alcoholic solution can be used, e.g. with 1,6-hexane diol.

The iron silicate zeolite is obtained e.g. from an iron compound, preferably Fe$_2$(SO$_4$)$_3$, and from a silicon compound, preferably also highly dispersed silicon dioxide, in aqueous amine solution, especially 1,6-hexane diamine, with or without the addition of alkali or alkaline earth metals at 100° to 200° C. under autogenous pressure as described e.g. in EP 0,007,081.

Alumino-, boro- and iron silicate zeolites of the pentasil type as well as the isotactic zeolites described in DE-OS 30 06 471 and EP 0,034,727 (both corresponding to U.S. Pat. No. 4,401,637 which is incorporated by reference in its entirety) and EP 0,046,504 are especially preferred.

The molecular sieves produced in this manner can be shaped into strands or tablets after their isolation, drying at 100° to 160° C., preferably 110° C., and calcining at 450° to 600° C., preferably 550° C., with a binding agent in a ratio of 90:10 to 40:60% by weight. Various aluminum oxides, preferably boehmite, amorphous aluminum silicates with an SiO$_2$/Al$_2$O$_3$ ratio of 25:75 to 95:5, preferably 75:25, silicon dioxide, preferably highly dispersed SiO$_2$, mixtures of highly dispersed SiO$_2$ and of highly dispersed Al$_2$O$_3$, highly dispersed TiO$_2$ as well as clay are suitable as binding agent. After the formation the extrudates or compacts are dried at 110° C. for 16 hours and calcined at 550° C.

Such catalysts can be produced in an especially advantageous manner in that the isolated molecular sieve is deformed directly after the drying and subjected only after the formation to calcining. However, the molecular sieves can also be used in pure form without binder as strands or tablets. This formation takes place with the addition of stranding or peptizing agents such as e.g. methyl cellulose, hexaethyl cellulose, oxalic acid, nitric acid, ammonia, amine, silicoester, graphite or their mixtures. The desired catalyst particle size can be obtained from the zeolites shaped into strands by grinding and sieving. For use in fluid beds particle sizes between 0.1 and 0.6 mm are suitable and particle sizes between 1 to 5 mm are used in fixed beds whereas powders are used with preference in liquid-phase batch reactors.

The special suitability of the MFI zeolites used in accordance with the present invention arises on account of a posttreatment following the known production methods.

This posttreatment results in symmetrically arranged "nests" of OH groups being produced on the inner and the outer surfaces of the zeolite.

Si— or other metallic atoms such as B, Fe, Ga are removed from the oxidic crystal lattice by a suitable treatment. The oxygen bonds released in this manner are saturated by hydrogen ions. The use of borosilicate zeolites as precursor is preferred.

If a trivalent element, e.g. B, which is to be dissolved out is concerned, symmetrically arranged silanol groups also result: in accordance with the following drawing:

The OH groups of the "nests" connected by hydrogen bridge formation can be demonstrated e.g. by FT-IR examinations. However, the formation of silanol nests is not limited solely to boron zeolite.

The geometric arrangement as well as the weakly acid behavior of the four silanol groups on the surface of the zeolite crystals surprisingly acts in an especially favorable manner on the rearrangement of cyclohexanone oxime to $\epsilon$-caprolactam in the gaseous phase. The suitable crystallite size for the method of the invention is <5 $\mu$m, preferably <2 $\mu$m, especially <1 $\mu$m. A range of 0.05–0.5 $\mu$m proves to be extremely advantageous.

If highly silicatic MFI zeolites such as e.g. silicalites with monoclinic structure are concerned, the latter is converted by a basic treatment at rather high temperatures into the orthorhombic structure. The structural transformation can be demonstrated e.g. by X-ray diffraction techniques. To this end the catalyst is brought into contact with a solution of ammonium salts (nitrate, chloride) and/or aqueous ammonia solution in an agitated flask or in an autoclave under autogenous pressure at a temperature of 20° to 150° C., preferably 60° to 150° C. The catalyst obtained in this manner is then dried at 110° C. for 12 hours. An orthorhombic crystalline structure with the active hydroxyl nests described is then obtained.

In the case of boron-containing MFI zeolites there is a significant possibility of modification by exposing the zeolitic material, shaped or not shaped, to a treatment with acids such as hydrochloric acid, hydrofluoric acid, phosphoric acid and/or water vapor. The procedure is such, for example, in this case that zeolites are treated in powder form with 0.5 to 3 N phosphoric acid for 0.5 to 10 hours at 40° to 100° C. After the 5 treatment they are washed with water, dried at 80° to 100° C. for 0.5 to 10 hours and calcined at 350° to 650° C. for 1 to 10 hours. According to another method of operation, zeolites are treated before or after their shaping with binding agents e.g. 1 to 3 hours at temperatures of 60° to 80° C. with a 3 to 25% by weight, especially 12–20% by weight, aqueous hydrochloric acid.

A preferred modification of MFI zeolites is described by the following:

If the zeolitic powder is treated with water vapor it is advantageous to work at a temperature of 300° to 650° C., quite especially preferably 400° to 500° C., for a period of 0.5 to 3 hours, preferably 1 to 2 hours, and to use a mixture of nitrogen or air and water vapor with a partial pressure of water vapor of 0.01 to 1 bar, preferably 0.05 to 0.8 bar, quite especially preferably 0.1 to 0.5 bar. This treatment can be followed by an acid treatment, e.g. with aqueous hydrochloric acid with a pH between 4 to 6, preferably 5 to 6. The zeolite treated in this manner is washed with water and dried at 110° C. for 16 hours.

A further preferred embodiment is the calcination of zeolites under oxygen at a temperature of 450° to 600° C., preferably at 500° to 550° C., in particular if one starts with boron and Fe zeolites. A demetallization or expulsion of elements from the lattice skeleton takes place wherein they remain as amorphous constituents in oxidic form in the pores.

After drying at 100° to 150° C., preferably at 110° to 120° C., and a calcination at 450° to 600° C., preferably at 500to 550° C., the zeolites can be tabletted or stranded with a binding agent in a ratio of 90:10 to 40:60% by weight. Various aluminum oxides, preferably boehmite, amorphous aluminosilicates with an $SiO_2/Al_2O_3$ ratio of 25:75 to 95:5, preferably 75:25, silicon dioxide, preferably highly dispersed $SiO_2$ mixtures of highly dispersed $SiO_2$ and highly dispersed $Al_2O_3$ as well as clay are suitable as binding agent. After the shaping step the extrudates or compacts are dried at 110° C. for 16 h and calcined at 550° C. for 16 h.

However, there is also the possibility of not subjecting the zeolites to a calcining until after the formation.

If the zeolites are used without binding agents as strands or tablets, then peptizing agents can be used for stabilizing the formation. The following are suitable examples of peptizing agents: ethyl cellulose, stearic acid, potato starch, formic acid, oxalic acid, acetic acid, nitric acid, ammonia, amines, silicoester and graphite or their mixtures.

The operating pressure is between 0.01 to 1 bar, preferably 0.05 to 0.5 bar, especially preferably 0.08 to 0.25 bar. A narrow temperature range around 300° C. and especially less than 300° C. is especially favorable at a pressure of 0.08 to 0.25 bar.

The loading of the catalyst with cyclohexanone oxime, expressed by the "weight hourly space velocity (kg/h oxime per kg catalyst), is WHSV=0.1 to 10 $h^{-1}$, preferably 0.2 to 5 $h^{-1}$. Water is used preferably in a ratio of >2.5 moles:1 (oxime). The reaction can be carried out in a fixed bed or a fluid bed.

In the fixed bed method the feed materials are mixed as a rule before they are passed via an evaporator into the reaction zone. Tabletted or extruded formed materials are used as catalysts, the average particle sizes of which can be between 0.5 and 5 mm.

In the fluidized bed process the individual components can be guided into the fluidized bed mixed or separately via a pre-evaporator or directly. Fluidized-bed material in extruded form with average diameters of 80 to 250 $\mu$m have proven to be especially favorable for this.

If the conversion drops below a set value after a certain test time the activity of the catalyst can be regained by a renewed calcining. The regeneration temperature is 350° to 650° C., preferably 400° to 550° C. and quite especially preferably 450to 500° C. The regeneration time is a function of the residual activity of the catalyst and is between 16 hours and 96 hours. Pure oxygen, air or, surprisingly, also pure nitrogen can be used for this purpose. If nitrogen is used as regeneration gas the treatment time is longer than if air is used.

The following examples illustrate the invention:

Description of the Catalysts

Catalyst A

| Batch: | (g) |
|---|---|
| SiO$_2$ (Aerosil 200) | 64.0 |
| B(OH)$_3$ | 12.2 |
| Hexamethylene diamine (50% solution in water) | 800.0 |

The hexamethylene diamine solution is placed in a PE beaker. The boric acid as the boron source is added thereto under agitation and the mixture agitated until the acid has completely dissolved. This solution is filled into an agitated autoclave and the SiO$_2$ added within 10 min under agitation. The matter is synthesized in the closed autoclave for 14 days at 170° C. with an agitator speed of 50 rpm. After the batch has cooled off it is removed from the autoclave. The supernatant solution is carefully decanted off and the remaining solid placed on a filter and thoroughly post-washed with deionized water. The product is dried for 12 h at 110° C. and then calcined 12 h at 550° C. under air.

Forming: 100 g of the catalytic powder is intimately mixed with an auxiliary forming aid and 100 g water. The resulting mixture is extruded at a pressure of 80 bar to strands with a diameter of 2 mm. The strands are dried for 12 h at 110° C. and calcined at 550° C. for 12 h. Comminution on a sieve with the desired mesh width and sieving of f of the fine component brings the catalyst particles to the proper particle size.

Catalyst B

| Batch | (g) |
|---|---|
| Silica sol (LUDOX) | 79.6 |
| Boric acid trimethyl ester | 3.9 |
| Tetrapropylammonium hydroxide | 22.2 |
| Deionized water | 89.0 |
| Ammonia solution (25% by weight) | 72.0 |

Silica sol, TPAOH, the deionized water and the boron source are placed in an agitated autoclave. The ammonia solution is added to the suspension. The matter is synthesized in the closed autoclave for 7 days at 185° C. with an agitator speed of 100 rpm. After the batch has cooled off it is removed from the autoclave. The supernatant solution is carefully decanted off and the remaining solid placed on a filter and thoroughly post-washed with deionized water. The product is dried for 12 h at 110° C. and then calcined 12 h at 550° C. under air.

Forming: The forming takes place as for catalyst A.

Catalyst C

| Batch: | (g) |
|---|---|
| SiO$_2$ (Aerosil) | 8.0 |
| B(OH)$_3$ | 3.39 |
| Tetrapropylammonium bromide | 8.61 |

Catalyst C -continued

| Batch: | (g) |
|---|---|
| Ammonium fluoride | 2.47 |
| Deionized water | 168.0 |

The deionized water is placed in a 200 ml PTFE beaker. The boric acid is dissolved in the water under agitation. Then ammonium fluoride is added at first and then TPABr added. Finally, SiO$_2$ is stirred in. The synthesis is carried out in the closed autoclave for eight days at 186° C. After the batch cools off the supernatant solution is carefully decanted off and the remaining solid placed on a filter and thoroughly post-washed with deionized water. The product is dried for 12 h at 110° C. and then calcined 12 h at 550° C. under air.

Forming: The shaping takes place in the same manner as for catalyst A.

Catalyst D

Commercially available HZSM-5 with Si/Al=54; ZEOCAT PZ-2/54H of the Uetikon company.

Catalyst E

Commercially available catalyst of the Degussa company; Aerosil 200. Characterization: SiO$_2$.

Catalyst F

| Batch: | (g) |
|---|---|
| Tetraethylorthosilicate | 500 |
| Ethanol | 1070 |
| Tetra-n-propylammonium hydroxide (10% solution in water) | 1120 |

Tetraethylorthosilicate, tetra-n-propylammonium hydroxide and ethanol are intensively mixed in a 5-liter steel autoclave for 120 min. The cover is then sealed and the solution brought to crystallization under strong agitation at 105° C. After 96 hours the synthesis is stopped, the catalyst washed, dried at 110° C./16 h and calcined at 550° C./12 h. Silicalite was obtained.

Forming: The shaping was carried out in the same way as for catalyst A.

Catalyst G 5 g of the unshaped catalyst F were agitated with a mixture of 5 g aqueous ammonium nitrate solution (7.5%) and 10 g aqueous ammonia (28%) for one hour in a 100 ml single-neck flask at room temperature. The catalyst was filtered off and subjected to the same procedure three additional times. The powder was then washed and dried. It was pressed to tablets and comminuted to particles with a particle size of 1–1.6 mm.

Catalyst H

Production as for catalyst G. However, the treatment is carried out in an autoclave at 90° C. under autogenous pressure.

Catalyst I 5 g of the powdery catalyst B are overflowed in a ceramic tube 4 cm in diameter at 400° C. by a nitrogen-water vapor mixture for 2 hours. The mass fraction of the water is approximately 50%. After the water-vapor treatment the catalyst is agitated in a 100 ml single-neck flask in an aqueous HCl solution (pH 6) at room temperature for 24 h. The drying takes place subsequently. The dried powder is pressed to tablets and comminuted to particles with a particle size of 1–16 mm.

Catalyst J

The production and forming of this catalyst take place as for catalyst I. However the water-vapor treatment is carried out at 550° C. pressure. After the water-vapor treatment the catalyst is agitated in a 100 ml single-neck flask in an aqueous HCl solution (pH 6) at room temperature for 24 h. The drying and forming take place subsequently as they were for catalyst I.

Description of the Testing System with Fixed-Bed Reactor

The catalytic examinations in the fixed bed were carried out in a tubular reactor with an inside diameter of 6 mm. The reaction zone was in a furnace which set a uniform temperature over the entire reaction stretch. At the end of the reaction zone a netting wire prevented the catalytic particles from being discharged. Cyclohexanone oxime was mixed with the solvents and any additive components in a receiving container and conducted via a minidosing pump into the pre-evaporator. Here the mixture was mixed with the carrier gas and conducted in gaseous form into the reactor. The reaction products were trapped in a cryogenic trap cooled with liquid nitrogen, thawed and subjected to an analysis by gas chromatography. The mass balances were approximately above 99%.

TABLE 1

Influence of the temperature and of the pressure decrease

| Example | Catalyst | Temp. | Pressure | WHSV | Conversion | Selectivity |
|---|---|---|---|---|---|---|
| 1* | A | 350° C. | 1 atm | 0.25 h$^{-1}$ | 100% [1] | 61% |
| 2* | D | 350° C. | 1 atm | 0.25 h$^{-1}$ | 99.6% [2] | 50.5% |
| 3* | A | 300° C. | 1 atm | 0.25 h$^{-1}$ | 100% [3] | 57.4% |
| 4* | A | 250° C. | 1 atm | 0.25 h$^{-1}$ | 100% [4] | 54.4% |
| 5* | A | 380° C. | 1 atm | 0.25 h$^{-1}$ | 100% [5] | 47% |
| 6 | A | 350° C. | 0.1 bar | 0.25 h$^{-1}$ | 99% | 76% |
| 7 | A | 300° C. | 0.1 bar | 0.25 h$^{-1}$ | 96% | 92% |

Feed material mixture toluene/cyclohexanone oxime 9:1 Mass fractions
Nitrogen current of 6 l/g
*Comparison examples:
[1] Conversion after 2 h, conversion decrease after 8 h < 1%
[2] Conversion after 2 h, conversion decrease after 8 h around 26%
[3] Conversion after 2 h, conversion decrease after 8 h at 22%
[4] Conversion after 2 h, conversion decrease after 8 h at 92%

EXAMPLE 8

Figure 1:
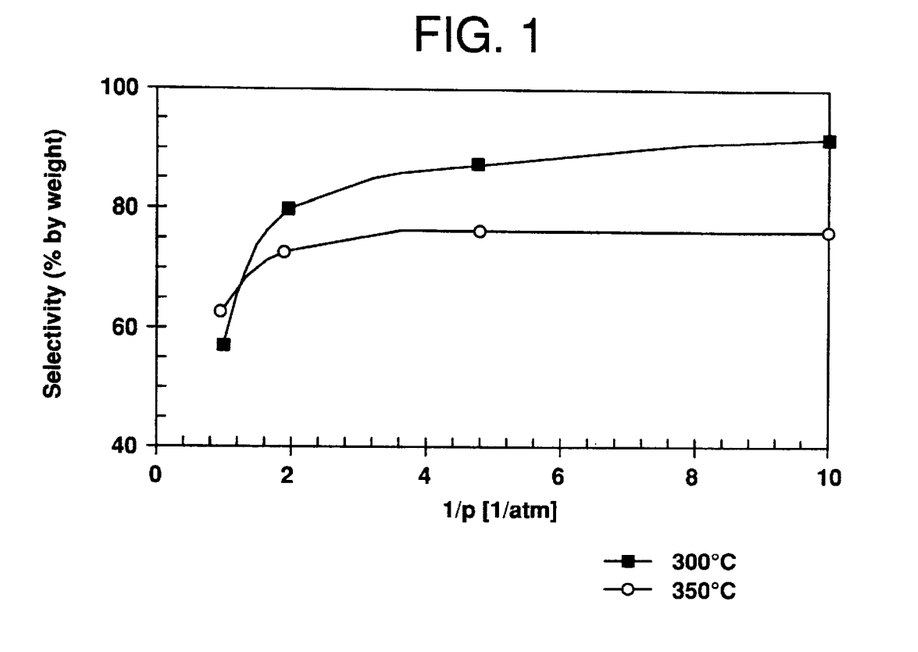
FIG. 1 shows the influence of pressure on selectivity at 300° C. and 350° C. (y-axis=Selectivity (% by weight)),. Catalyst A; WHSV=0.25 h$^{-1}$; T=2 h; Toluene/oxime=9:1.

FIG. 1 shows the influence of the pressure decrease at 300° C. and 350° C. (y-axis=Selectivity (% by weight)), Catalyst A; WHSV=0.25 h$^{-1}$; T=2 h; Toluene/oxime=9:1.

EXAMPLE 9

Figure 2:
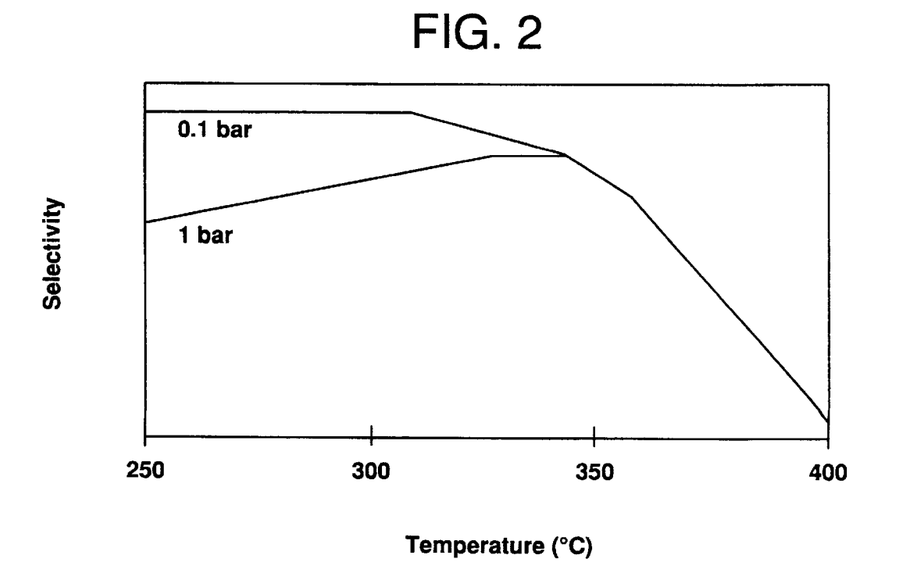
FIG. 2 shows the influence of the temperature at 0.1 and 1 bar (y-axis=Selectivity) on selectivity.

FIG. 2 shows the influence of the temperature at 0.1 and 1 bar (y-axis=Selectivity). The path of curves show qualitatively the influence of pressure and temperature on the selectivity.

EXAMPLES 10–12

TABLE 2

Influence of the residence time and pressure on the reaction

| Example | Pressure | Nitrogen current | Residence time | Selectivity |
|---|---|---|---|---|
| 10 | 1.0 bar abs | 5 l/h | 1.1 s | 62.9% |
| 11 | 1.0 bar abs | 30.9 l/h | 0.4 s | 68.0% |
| 12 | 0.2 bar abs | 3.8 l/h | 0.4 s | 75.9% |

Catalyst A; WHSV=0.25 h$^{-1}$; t=2 h; Toluene/oxime=9:1

EXAMPLES 13–17

TABLE 3

Influence of various solvents on the reaction at 300° C. and vacuum

| Example | Solvent (LM) | 2 h Conversion (%) | 2 h Selectivity (%) | 8 h Conversion (%) | 8 h Selectivity (%) |
|---|---|---|---|---|---|
| 13 | toluene | 98.2 | 90.8 | 38.5 | 81.0 |
| 14 | benzene | 100 | 87.8 | 44.8 | 81.9 |
| 15 | methanol | 97.1 | 93.4 | 53.3 | 91.2 |
| 16 | ethanol | 97.3 | 89.3 | 94.1 | 94.0 |
| 17 | tert. butanal | 100 | 91.0 | 99.0 | 90.2 |

Catalyst A; T=300° C.; p=0.1 bar; WHSV=0.25 h$^{-1}$; solvent/oxime=9:1

EXAMPLE 18

Figure 3:
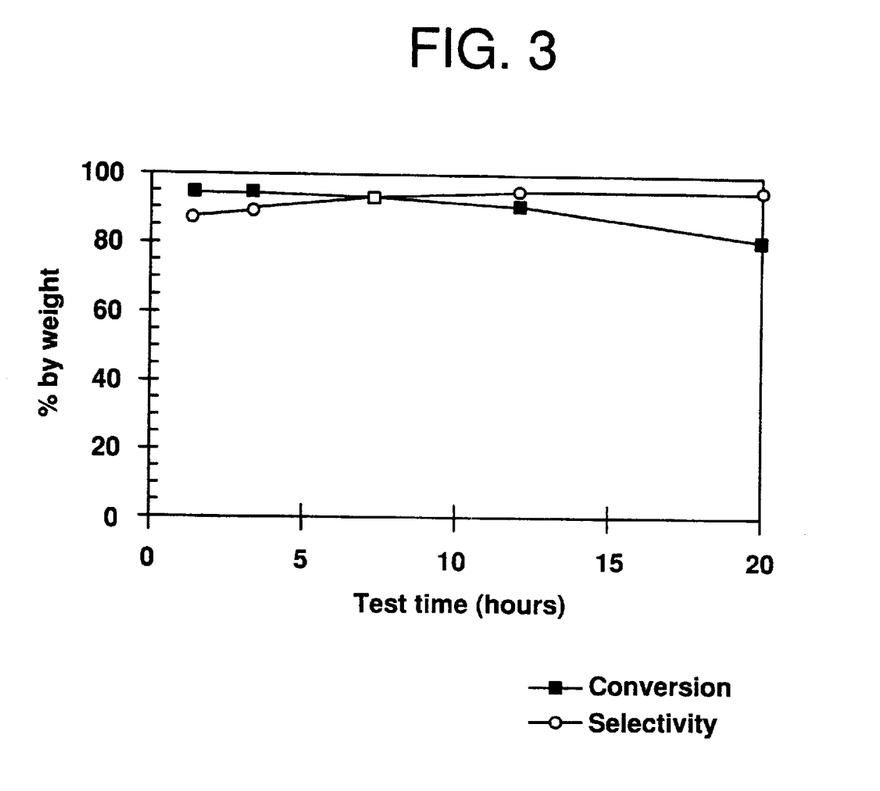
FIG. 3 shows the course of conversion and selectivity over 20 hours (% by weight vs. test time (hours)); solid squares represent conversion, hollow dots represent selectivity; Catalyst A; T=300° C.; p=0.1 bar; WHSV=0.25 h$^{-1}$; ethanol/oxime=9:1.

FIG. 3 shows the course of conversion and selectivity over 20 hours (% by weight vs. test time (hours)); Catalyst A; T=300° C.; p=0.1 bar; WHSV=0.25 h$^{-1}$; ethanol/oxime=9:1.

EXAMPLES 19–24

TABLE 4

Influence of added water and vacuum in the presence of ethanol

| Example | Addition of water mole/ mole oxime | Conversion (t = 1 h) | Selectivity | Conversion decrease after 8 hours |
|---|---|---|---|---|
| 19 | 0 | 97.3% | 92% | 3% |
| 20 | 0.62 | 97.8% | 92% | 1.5% |
| 21 | 3.1 | 97.8% | 92% | <1% |
| 22 | 6.2 | 89.2% | 93% | <1% |

Catalyst A; T=300° C.; p 0.1 bar WHSV=0.25 h$^{-1}$; ethanol/oxime=9:1

TABLE 5

Influence of added water and vacuum in the presence of methanol

| Example | Addition of water mole/ mole oxime | Conversion (t = 1 h) | Selectivity | Conversion decrease after 8 hours |
|---|---|---|---|---|
| 23 | 0 | 97.1% | 92% | 44% |
| 24 | 3 | 97.4% | 92% | 4% |

Catalyst A; T=300° C.; p=0.1 bar; WHSV=0.25 h$^{-1}$; methanol/oxime=9:1

EXAMPLE 25

Figure 4:
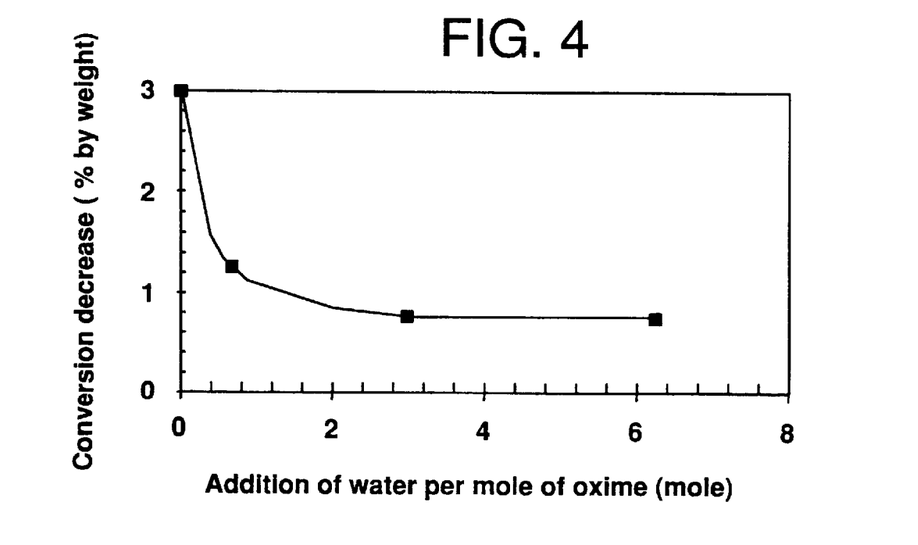
FIG. 4 shows the influence of water on the service life of the catalyst (Conversion decrease (% by weight) vs. addition of water per mole oxime (mole)); Catalyst A; T=300° C.; p=0.1 bar; WHSV=0.25 h$^{-1}$; ethanol/oxime=9:1.
Figure 5A:
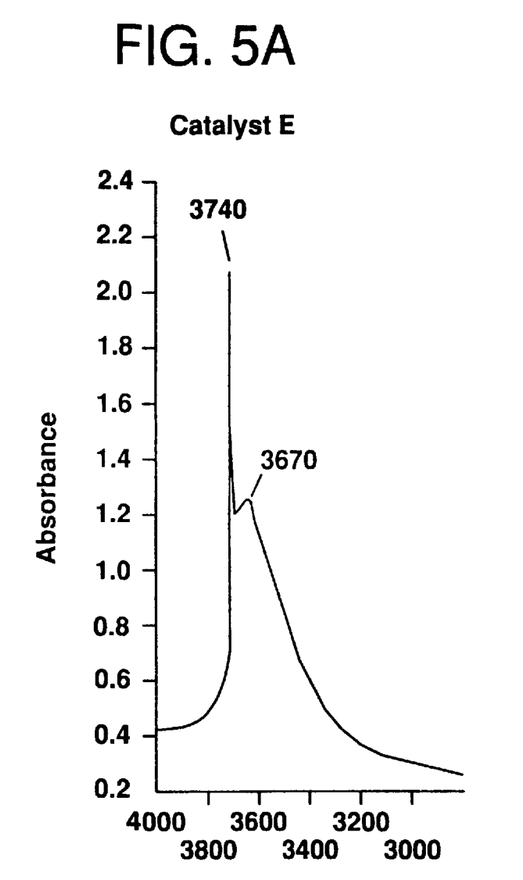
FIG. 5 shows the frequencies of the individual silanol groups in the FT-IR examination of catalysts E, F, G and H.
Figure 5B:
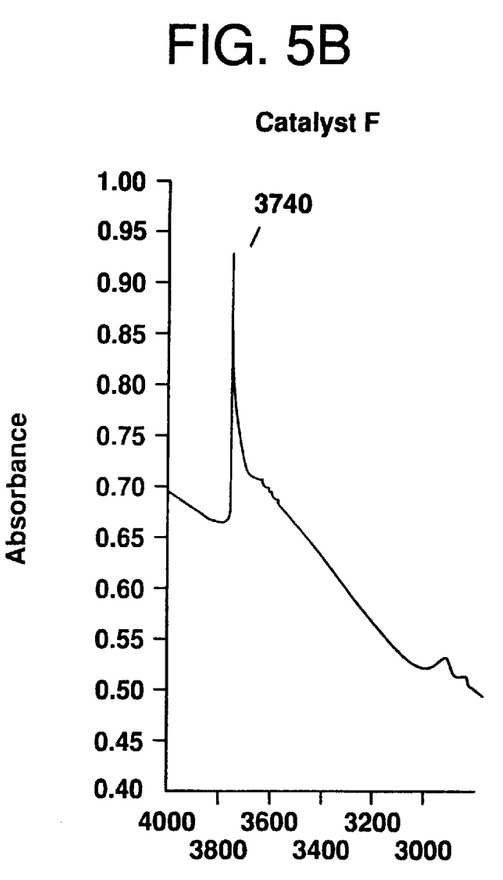
Figure 5C:
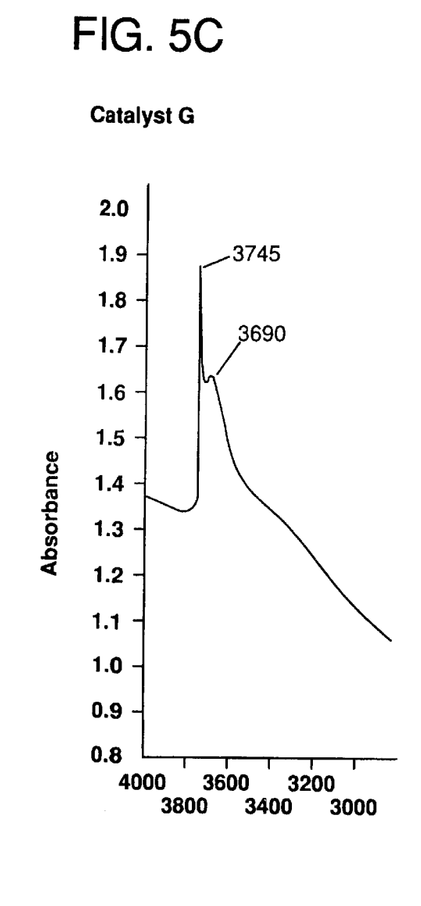
Figure 5D:
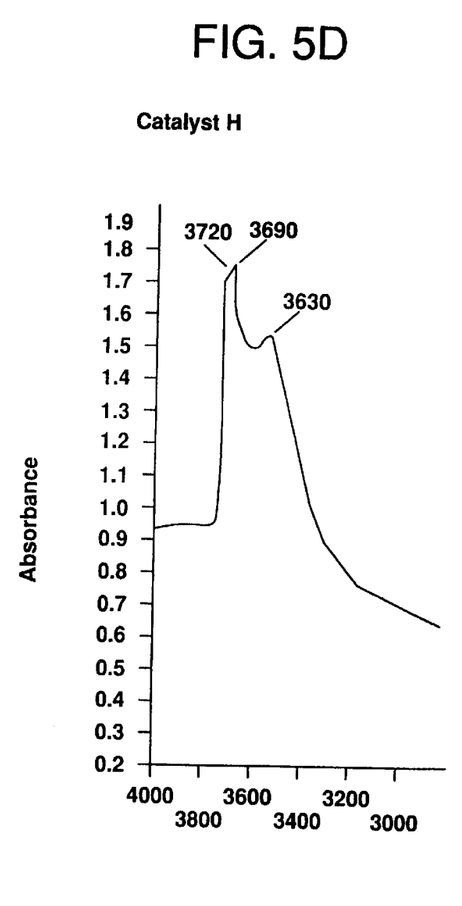

FIG. 4 shows the influence of water on the service life of the catalyst (Conversion decrease (% by weight) vs. addition of water per mole oxime (mole)); Catalyst A; T=300° C.; p=0.1 bar; WHSV=0.25 $h^{-1}$; ethanol/oxime=9:1.

EXAMPLES 26–28

TABLE 6

Influence of the crystallite size

| Catalyst | Crystallite size | Test Time (h) | Conversion (% by wt.) | Selectivity (% by wt.) |
|---|---|---|---|---|
| A | <<1 mm | 1 | 99.8 | 87.8 |
|   |        | 6 | 99.8 | 89.3 |
| B | 10–20 mm | 1 | 53.8 | 62.8 |
|   |        | 6 | 23.3 | 72.2 |
| C | 10 × 100 mm | 1 | 43.1 | 64.7 |
|   |        | 6 | 21.3 | 64.9 |

Catalyst A; T=350° C.; p=1 atm; WHSV=0.25 $h^{-1}$; ethanol/oxime=9:1

EXAMPLE 29

This example shows the regeneration with oxygen:

TABLE 7

Conversion and selectivity after several regeneration cycles

| Test days | Test time (h) | Conversion (% by wt.) | Selectivity (% by wt.) |
|---|---|---|---|
| 1 | 1 | 98.6 | 88.5 |
|   | 6 | 98.4 | 91.3 |
| 2 | 1 | 99.3 | 88.9 |
|   | 6 | 98.9 | 91.7 |
| 5 | 1 | 99.7 | 89.0 |
|   | 6 | 97.8 | 93.0 |
| 10 | 1 | 99.6 | 91.1 |
|   | 6 | 97.5 | 92.3 |
| 15 | 1 | 97.8 | 89.2 |
|   | 6 | 97.2 | 90.7 |
| 20 | 1 | 98.8 | 91.2 |
|   | 6 | 96.9 | 92.0 |

Catalyst A;
Test conditions: T=300° C.; p=0.1 bar; WHSV=0.25 $h^{-1}$; solvent=ethanol
Regeneration conditions: T=500° C.; p=1 atm; Air current=5 l/h; t=16 h

EXAMPLE 30

This example shows the regeneration with nitrogen:

TABLE 8

Conversion and selectivity after several regeneration cycles

| Test days | Test time (h) | Conversion (% by wt.) | Selectivity (% by wt.) |
|---|---|---|---|
| 1 | 1 | 98.7 | 88.6 |
|   | 6 | 95.1 | 90.7 |
| 2 | 1 | 94.1 | 90.0 |
|   | 6 | 93.7 | 92.3 |
| 3 | 1 | 91.1 | 89.0 |
|   | 6 | 89.5 | 91.3 |
| 4 | 1 | 87.6 | 91.0 |
|   | 6 | 85.5 | 92.3 |

TABLE 8-continued

Conversion and selectivity after several regeneration cycles

| Test days | Test time (h) | Conversion (% by wt.) | Selectivity (% by wt.) |
|---|---|---|---|
| regeneration time raised to 40 h | | | |
| 5 | 1 | 96.3 | 79.5 |
|   | 6 | 90.9 | 93.7 |
| regeneration temperature raised to 500° C., regeneration time 16 h | | | |
| 6 | 1 | 100 | 86.0 |
|   | 6 | 97.5 | 91.1 |

Catalyst: A;
Test cond.: T=300° C.; p=0.1 bar; WHSV=0.25 $h^{-1}$; solvent=ethanol.
Regeneration cond.: T=500° C.; p=1 atm;
Air current=5 l/h; t=16 h

EXAMPLES 31* and 32*

TABLE 9

Conversion and selectivity on highly silicalitic catalysts (Comparative examples)

| Catalyst Test time (h) | E Conversion (% by wt.) | E Selectivity (% by wt.) | F Conversion (% by wt.) | F Selectivity (% by wt.) |
|---|---|---|---|---|
| 1 | 32.8 | 54.0 | 46.9 | 29.8 |
| 3 | 23.3 | 62.9 | 40.1 | 26.8 |
| 6 | 18.4 | 64.1 | 33.3 | 24.4 |

T=300° C.; p=0.1 bar; WHSV=0.25 $h^{-1}$; solvent=ethanol

EXAMPLES 33 and 34

Catalyst F was treated as follows: The catalytic particles were agitated, washed and dried at 110° C. to this end in a solution of aqueous ammonia and ammonium nitrate three times for one hour. This treatment measure was carried out on the one hand in a single-neck flask at room temperature (example 33) and on the other hand in an autoclave at 90° C. under autogenous pressure (example 34). The test results achieved with the treated catalysts are shown in table 10.

TABLE 10

Conversion and selectivity of the modified highly silicalitic MFI zeolite (silicalite)

| Catalyst Test time (h) | G Conversion (% by wt.) | G Selectivity (% by wt.) | H Conversion (% by wt.) | H Selectivity (% by wt.) |
|---|---|---|---|---|
| 2 | 57.7 | 19.8 | 76.0 | 93.1 |
| 4 | 49.0 | 19.5 | 74.6 | 92.3 |
| 6 | 23.3 | 14.7 | 67.1 | 91.8 |

T=300° C.; p=0.1 bar; WHSV=0.25 $h^{-1}$; solvent=ethanol
Characterization of the catalysts E, F, G, R with FT-IR (see also FIG. 5):

terminal        geminal        vicinal bridges

-continued silanol nest

Frequencies of the individual silanol groups in the FT-IR:
terminal →n=3745±5 cm$^{-1}$
geminal →n=3725 cm$^{-1}$
vicinal bridges →n=3725 u. 3500 cm$^{-1}$
silanol nest →n=3500 cm$^{-1}$

EXAMPLES 35–37

These examples show the influence of the water vapor and acid treatment on the catalytic activity and selectivity.

TABLE 11

Catalytic treatment with water vapor (2 h) and aqueous HCl solution (pH 4; 24 h)

| Catalyst | Treatment temperature | Test time (h) | Conversion (% by wt.) | Selectivity (% by wt.) |
|---|---|---|---|---|
| B | untreated | 1 | 32.8 | 56.8 |
|   |   | 3 | 22.3 | 51.9 |
|   |   | 6 | 19.8 | 51.1 |
| I | 400° C. | 1 | 48.0 | 61.9 |
|   |   | 3 | 26.4 | 60.9 |
|   |   | 6 | 18.7 | 68.9 |
| J | 500° C. | 1 | 47.6 | 66.3 |
|   |   | 3 | 29.2 | 65.9 |
|   |   | 6 | 21.2 | 68.8 |

T=350° C.; p=1 atm; WHSV=0.25 h$^{-1}$; solvent=ethanol

Description of the testing system with fluid-bed reactor:

A vortex reactor with an inside diameter of 51 mm and a vortex zone of 600 mm was used in the fluid-bed method. The catalysts rested on a glass frit with pore widths below 30 μm. Cyclohexanone oxime was mixed with the solvents and any added components in a receiving container and conducted via a minidosing pump into the pre-evaporator. There the mixture was mixed with the carrier gas and conducted in gaseous form into the reactor. However, the mixture was also able to be injected directly into the vortex zone. The reaction products were conducted over a water-cooled condenser and then the non-condensed components were caught in a cold trap cooled with liquid nitrogen. For purposes of analysis a partial current of gas was discharged directly from the settling zone of the vortex reactor and examined by gas chromatography.

EXAMPLES 38 and 39

Figure 6:
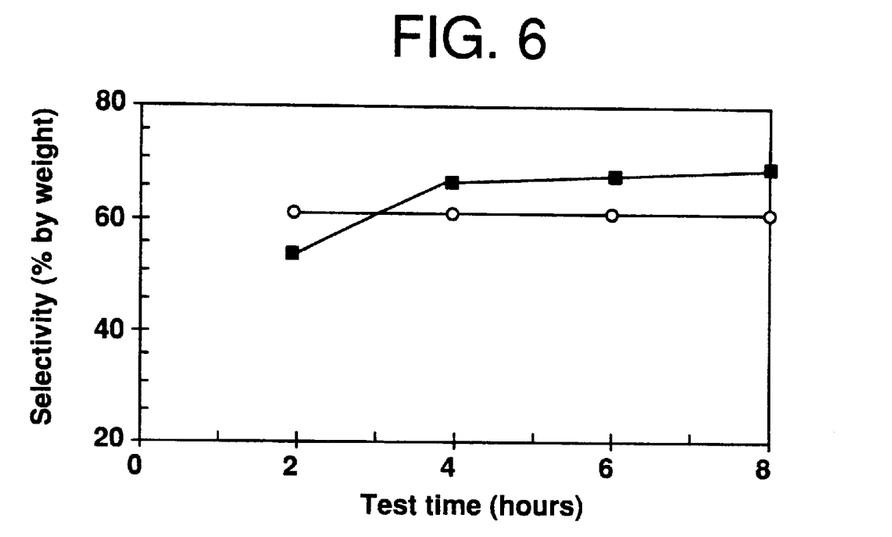
FIG. 6 shows the influence of the supply of educt on the selectivity for $\epsilon$-caprolactam (Selectivity (% by weight) vs. Test time (h)); Catalyst A; solvent=ethanol; hollow dots represent supply of educt via pre-evaporator (example 38) and solid squares represent direct injection into the fluid bed (example 39)

FIG. 6 shows the influence of the supply of educt on the selectivity for ε-caprolactam (Selectivity (% by weight) vs. Test time (h)); Catalyst A; p=1 atm; WHSV=0.05 h$^{-1}$; Z=8.2; solvent=ethanol, T=350° C. The conversion is 100% by weight in both examples.

EXAMPLES 40–42

Figure 7:
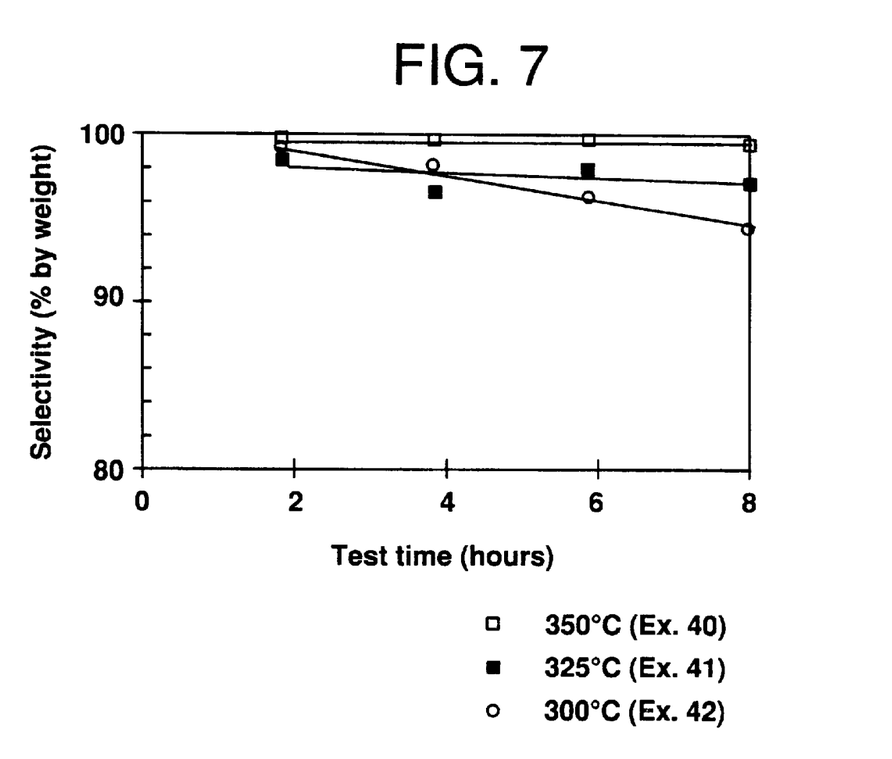
FIG. 7 shows the influence of the temperature on the conversion of cyclohexanone oxime (Conversion (% by weight) vs. Test time (h)); Catalyst A; p=1 atm; WHSV=0.05 h$^{-1}$; Z=8.2; solvent=ethanol; □ 350° C. (ex. 40); ■ 325° C. (ex. 41); 0 300° C. (ex. 42)

FIG. 7 shows the influence of the temperature on the conversion of cyclohexanone oxime (Conversion (% by weight) vs. Test time (h)); Catalyst A; p=1 atm; WHSV=0.05 h$^{-1}$; Z=8.2; solvent=ethanol.

Figure 8:
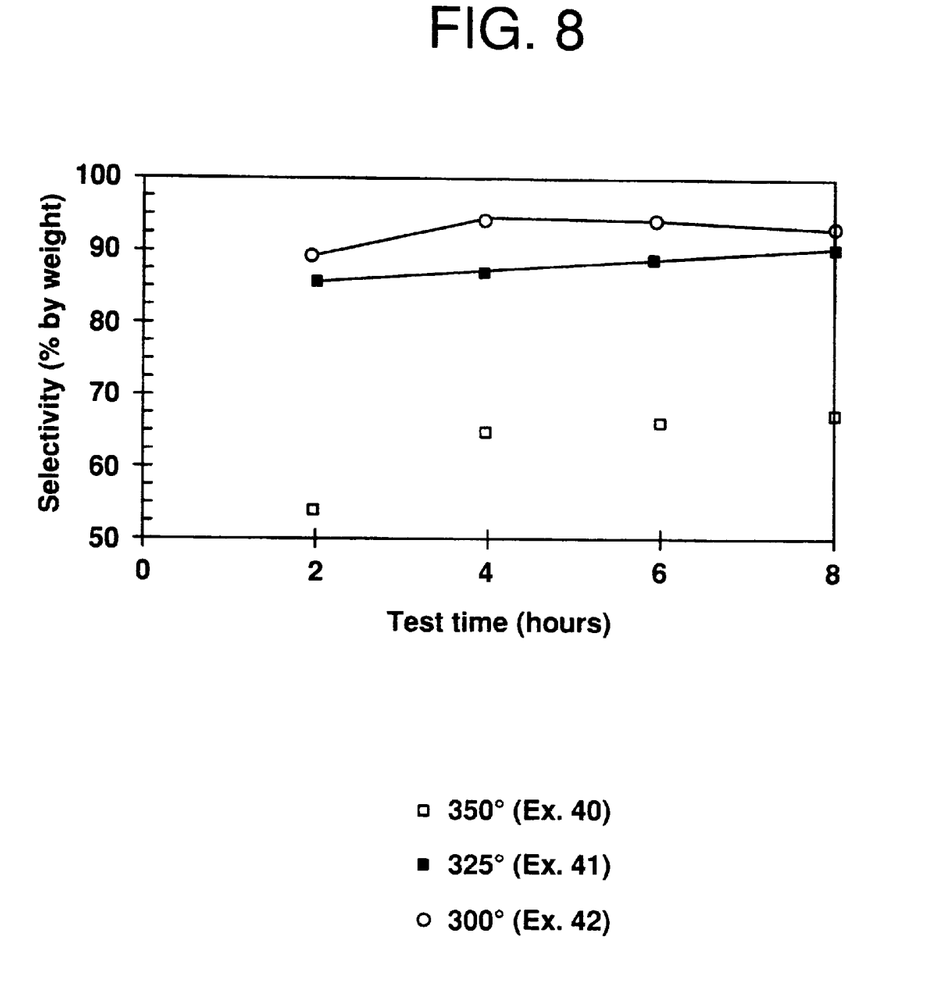
FIG. 8 shows the influence of the temperature on the selectivity for $\epsilon$-caprolactam (Selectivity (% by weight) vs. Test time (h)); Catalyst A; p=1 atm; WHSV=0.05 h$^{-1}$; Z=8.2; solvent=ethanol; □ 350° C. (ex. 40); ■ 325° C. (ex. 41); 0 300° C. (ex. 42).

FIG. 8 shows the influence of the temperature on the selectivity for ε-caprolactam (Selectivity (% by weight) vs. Test time (h)); Catalyst A; p=1 atm; WHSV=0.05 h$^{-1}$; Z=8.2; solvent=ethanol.

EXAMPLES 43–45

TABLE 12

Conversion and selectivity upon the addition of water to the educt

| Example | Addition of water (mole/mole oxime) | Test time (h) | Conversion (% by wt.) | Selectivity (% by wt.) |
|---|---|---|---|---|
| 43 | 0 | 1 | 97.8 | 88.0 |
|    |   | 8 | 96.9 | 91.1 |
| 44 | 3.1 | 1 | 99.5 | 88.0 |
|    |     | 8 | 96.9 | 92.1 |
| 45 | 8.3 | 1 | 99.3 | 87.2 |
|    |     | 8 | 98.4 | 92.5 |

Catalyst A; T=350° C.; p 1 atm; WHSV=0.08 h$^{-1}$; Z=12.8; solvent=ethanol

Further variations and modifications of the foregoing will be apparent to those skilled in the art and such variations and modifications are intended to be encompassed by the claims that are appended hereto.

German Priority Application 195 16 284.6 filed on May 4, 1995 and German Priority Application 196 08 660.4 filed on Mar. 6, 1996 are relied on and incorporated by reference in their entirety.

We claim:

1. A method of producing MFI zeolitic catalysts for use in producing ε-caprolactam, comprising:

contacting a MFI zeolite having central metal or semi-metal atoms including boron at a temperature of 20° to 150° C. under autogenous pressure in an autoclave with a solution of ammonia salts and/or aqueous ammonia solution to thereby remove some or all of said central metal or semi-metal atoms, wherein the resulting MFI zeolite catalysts have OH groups symmetrically arranged in relation to each other on the surface of the MFI zeolite catalysts due to a lack of central metal or semi-metal atoms, treating said boron-containing MFI zeolite at a temperature of 300° to 650° C. with water vapor for about 0.5 to about 3 hours and optionally treating with an acid treatment at a pH of 4 to 6, washing with water, and drying at about 110° for between about 12 and about 16 hours.

2. The method according to claim 1, further comprising separating a resulting orthorhombic product and drying.

3. The method according to claim 1, wherein said central metal or semi-metal atoms comprise at least one member selected from the group consisting of Si, Al, B, Fe, Ga, Cr, Be, As, Sb, Bi, Ge, Ti, Zr and Hf.

4. The method according to claim 3, wherein a ratio of Si:B is between 5 to 40:1.

5. The method according to claim 1, wherein said central metal atoms are B.

6. The method according to claim 1, wherein said MFI zeolite comprises a silicalite with monoclinic structure.

7. The method according to claim 1, wherein the contacting temperature is from 60° to 150° C.

8. The method according to claim 1, wherein said drying is at a temperature of about 110° C. for about 12 hours.

9. The method according to claim 1, wherein the optional acid treatment is at a pH from 5 to 6.

10. The method according to claim 1, wherein the water vapor treatment temperature is from 400° to 500° C.

11. The method according to claim 1, wherein said treating at a temperature of 300° to 650° C. with water vapor is for a period of from about 1 to about 2 hours.

12. The method according to claim 1, wherein said water vapor comprises a mixture with nitrogen or air.

13. The method according to claim 1, wherein said water vapor exhibits a partial pressure of water vapor of from 0.01 to 1 bar.

14. The method according to claim 13, wherein said partial pressure of water vapor is from 0.05 to 0.8 bar.

15. The method according to claim 14, wherein said partial pressure of water vapor is from 0.1 to 0.5 bar.

16. The method according to claim 1, further comprising treating said boron-containing MFI zeolite at a temperature of 60° to 80° C. with a 3 to 25% by weight aqueous acid and subsequently washing and drying at 400° to 500° C.

* * * * *